United States Patent
Sandrin et al.

(10) Patent No.: US 11,464,498 B2
(45) Date of Patent: Oct. 11, 2022

(54) METHOD FOR AUTOMATICALLY SELECTING A DEPTH RANGE FOR CALCULATING A PROPERTY OF A VISCOELASTIC MEDIUM

(71) Applicant: ECHOSENS, Paris (FR)

(72) Inventors: Laurent Sandrin, Bourg-la-Reine (FR); Michel Clet, Paris (FR)

(73) Assignee: ECHOSENS, Paris (FR)

( * ) Notice: Subject to any disclaimer, the term of this patent is extended or adjusted under 35 U.S.C. 154(b) by 11 days.

(21) Appl. No.: 17/282,221

(22) PCT Filed: Oct. 1, 2019

(86) PCT No.: PCT/EP2019/076616
§ 371 (c)(1),
(2) Date: Apr. 1, 2021

(87) PCT Pub. No.: WO2020/070139
PCT Pub. Date: Apr. 9, 2020

(65) Prior Publication Data
US 2021/0330297 A1    Oct. 28, 2021

(30) Foreign Application Priority Data

Oct. 2, 2018 (FR) ...................................... 1859096

(51) Int. Cl.
*A61B 8/00* (2006.01)
*A61B 8/08* (2006.01)
(52) U.S. Cl.
CPC .............. *A61B 8/585* (2013.01); *A61B 8/485* (2013.01)

(58) Field of Classification Search
CPC ............ A61B 8/08; A61B 8/485; A61B 8/585
See application file for complete search history.

(56) References Cited

U.S. PATENT DOCUMENTS

2007/0093716 A1    4/2007  Radulescu
2018/0098752 A1*   4/2018  Rouze .................... A61B 8/485

FOREIGN PATENT DOCUMENTS

JP    2016-007315 A    1/2016

OTHER PUBLICATIONS

Sandrin, L., et al., "Transient Elastography: A New Noninvasive Method for Assessment of Hepatic Fibrosis" Ultrasound in Medicine and Biology, vol. 29, No. 12, pp. 1705-1713, 2003.
(Continued)

*Primary Examiner* — Mark D Remaly
(74) *Attorney, Agent, or Firm* — Pillsbury Winthrop Shaw Pittman LLP

(57) ABSTRACT

A method for automatically selecting a calculation depth range upon measuring a property of a viscoelastic medium, the depth range being selected from P possible ranges, includes calculating, from the ultrasound signal acquired using a probe for elastography, the property of the viscoelastic medium in at least one of the P depth ranges as well as the distance between the probe and the wall of the viscoelastic medium; determining the validity of at least one of the P calculation depth ranges; determining the validity of the calculation of the property of the viscoelastic medium over the valid calculation depth range or ranges; selecting, from the values of the property of the viscoelastic medium the calculation of which is valid at the valid depth ranges, a depth range fulfilling a selection criterion.

19 Claims, 10 Drawing Sheets

(56) References Cited

OTHER PUBLICATIONS

International Search Report as issued in International Patent Application No. PCT/EP2019/076616, dated Nov. 4, 2019.
Varghese, T., "A Theoretical Framework for Performance Characterization of Elastography: The Strain Filter," IEEE Transactions on Ultrasonics, Ferroelectrics, and Frequency Control, vol. 44, No. 1, Jan. 1997, XP011437533, pp. 164-172.

\* cited by examiner

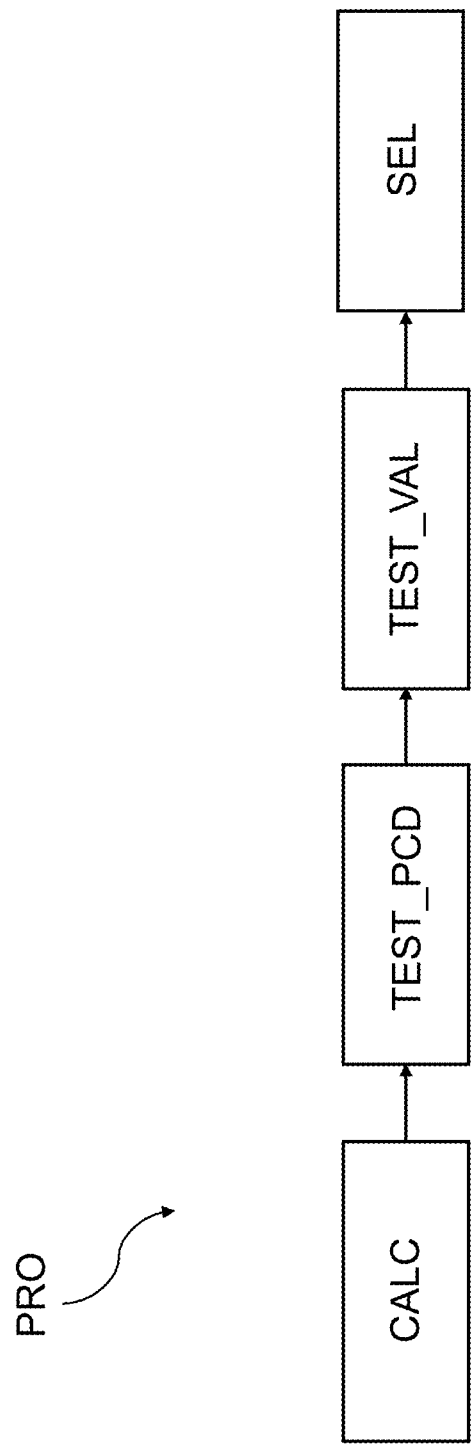

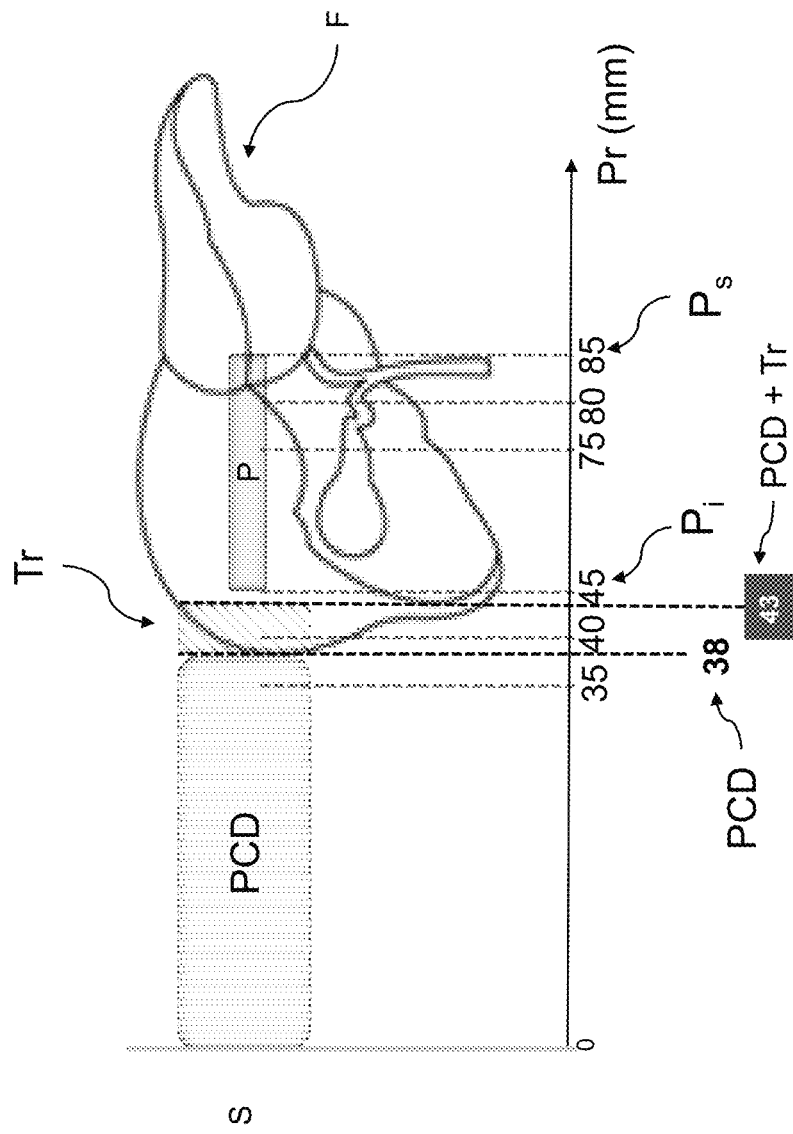

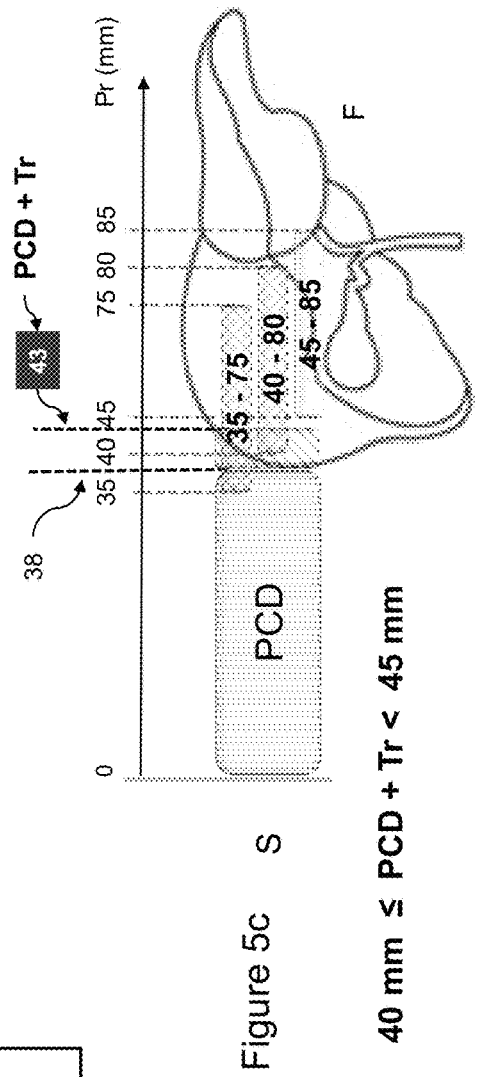
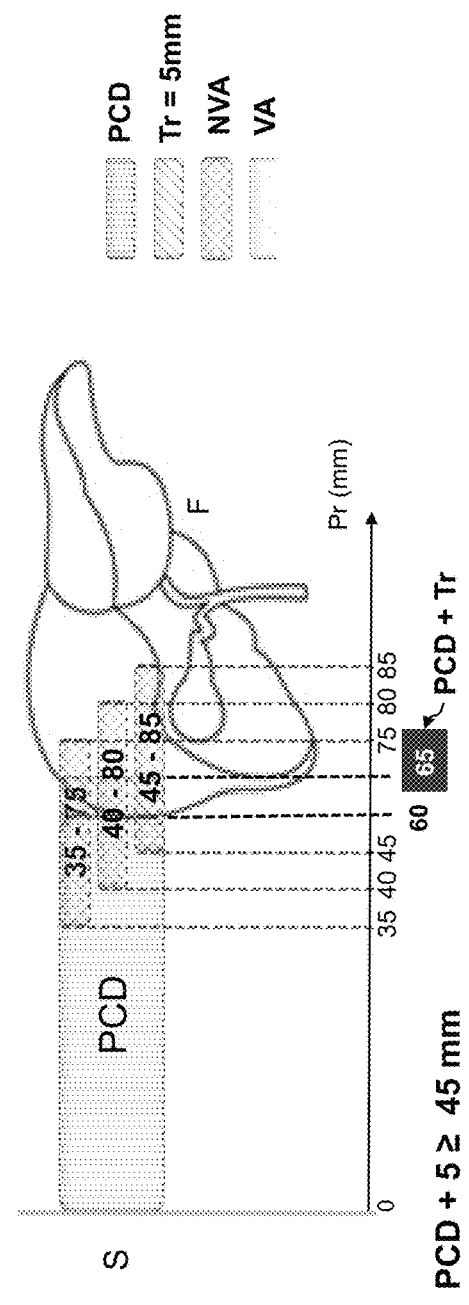
Figure 5c
Figure 5d

METHOD FOR AUTOMATICALLY SELECTING A DEPTH RANGE FOR CALCULATING A PROPERTY OF A VISCOELASTIC MEDIUM

CROSS-REFERENCE TO RELATED APPLICATIONS

This application is the U.S. National Stage of PCT/EP2019/076616, filed Oct. 1, 2019, which in turn claims priority to French patent application number 1859096 filed Oct. 2, 2018. The content of these applications are incorporated herein by reference in their entireties.

TECHNICAL FIELD

The present invention belongs to the field of elastography for the measurement of at least one property of a viscoelastic medium. An aspect of the present invention concerns a method for automatically selecting a calculation depth range upon measuring a property of a viscoelastic medium. The method according to the invention makes it possible to increase the speed, reliability and reproducibility of the measurement by selecting the depth range that fulfills a predetermined selection criterion. A second aspect of the invention concerns a method for the global measurement of at least one property of a viscoelastic medium in which the calculation depth range or ranges are selected automatically using the automatic selection method according to the invention. A third aspect of the invention concerns a device for measuring a property of a viscoelastic medium with automatic selection of the calculation depth range.

STATE OF THE ART

Transient elastography (also called pulse elastography) is one of the best known and most effective methods for determining the elasticity of a viscoelastic medium. For example, transient elastography is commonly used to determine the elasticity of the liver in humans or animals.

In transient elastography, a shear wave pulse is generated and its speed of propagation within the viscoelastic medium of interest is measured. The speed of propagation of the shear wave is then used to calculate the Young's modulus of the medium and thus to measure its elasticity.

There are several techniques for implementing transient elastography.

For example, the applicant has developed and marketed a Vibration Controlled Transient Elastography (VCTE) technique. The device using this technique, called Fibroscan®, is capable of measuring the elasticity of the human liver in a fast, non-invasive and reproducible way. In such a device for transient elastography, the shear wave is generated by a vibrator placed in contact with the medium to be characterised. The propagation of the shear wave is then tracked by a series of ultrasound acquisitions carried out by an ultrasound transducer with a high repetition rate. Each ultrasound acquisition corresponds to at least one ultrasound emission. Each ultrasound emission can be associated with the on-the-fly detection and recording of echoes generated by reflecting particles present in the medium under study for a defined range of depths. The reflected ultrasound signals are processed by correlation to deduce the tissue movements caused by the propagation of the shear wave, as a function of time and position in the medium. The study of these movements enables to deduce the speed of propagation of the shear wave within the viscoelastic medium, and thus the tissue elasticity, as explained in "Transient Elastography: a new noninvasive method for assessment of hepatic fibrosis" by L. Sandrin et al, published in Ultrasound in Medicine and Biology, Vol. 29, pages 1705-1713, 2003.

In the case of measuring a viscoelastic property of a medium such as a human liver, it is necessary to select the portion of reflected ultrasound waves corresponding to the depth at which the medium is located.

This selection operation is complicated by the fact that this depth varies greatly according to the morphology of the patient. For example, in the case of an obese patient, the viscoelastic medium to be analysed is more likely to be at a greater depth than in the case of a patient with normal morphology.

For this reason, in the case of an elasticity measurement using Fibroscan®, several calculation depth ranges are possible. FIG. 1 represents the distribution of the ultrasound sound power inside the patient's body for a probe with an S size as a function of the depth Pr inside the body. It is possible for example to select a calculation depth range from two possible ranges S1 and S2. S1 corresponds to the depth range between 15 mm and 40 mm. S2 corresponds to the depth range from 20 to 50 mm.

FIG. 2 illustrates the case of measuring a liver property using a depth range between 35 mm and 75 mm. In the example of FIG. 2, the distance between the probe and the external wall of the liver (or probe-to-capsula distance, PCD) is 38 mm. If the depth range at which the property is calculated is between 35 mm and 75 mm, this is not optimal because it is not completely included inside the liver. In particular, the presence of the external wall of the liver or liver capsula within the calculation range may distort the measurement.

In solutions currently known to those skilled in the art, the depth at which a viscoelastic property is to be calculated is fixed or left to the operator's choice. This may distort the measurement, if the fixed depth range is not adapted to the patient's morphology, or make it operator's dependent thereby reducing its reliability and reproducibility.

In addition, a change of depth range by the operator causes all measurements to be erased. As a result, the duration of the examination can increase substantially.

In other words, existing technical solutions do not allow an optimal and automatic selection of the calculation depth range when measuring a property of a viscoelastic medium such as human or animal liver.

GENERAL SUMMARY OF THE INVENTION

In order to at least partially solve problems of the state of the art, an object of the present invention is a method for automatically selecting a depth range for calculating a property of a viscoelastic medium, the depth range being selected from P possible ranges, P being an integer number greater than or equal to 2, said method comprising the following steps of:

Calculating, from an ultrasound signal acquired using a probe for elastography, the value of the property of the viscoelastic medium in at least one of the P possible depth ranges, and the distance between the probe and the wall delimiting the viscoelastic medium;

Determining the validity of at least one of the P calculation depth ranges, a calculation depth range being considered as valid if it fulfills a validity criterion calculated from the distance between the probe and the wall delimiting the viscoelastic medium;

Determining the validity of the calculation of the property of the viscoelastic medium over the valid calculation depth range or ranges, said calculation of the value being considered as valid if it fulfills a validity criterion calculated from the quality of an elastogram;

Selecting, from among the valid depth ranges that comprise at least one value of the property of the viscoelastic medium the calculation of which is valid, a depth range fulfilling a predetermined selection criterion.

By property of a viscoelastic medium it is meant a viscoelastic or ultrasound property of the viscoelastic medium. An example of a viscoelastic property is the speed of propagation of a shear wave within the viscoelastic medium. Another example of a viscoelastic property of the medium is the elasticity of the viscoelastic medium. An example of an ultrasound property of the viscoelastic medium is an ultrasound attenuation parameter within the viscoelastic medium.

By probe for elastography it is meant a probe with at least one ultrasound transducer. This probe can be used to make measurements of the viscoelastic properties of a medium. An example of a probe for elastography is a probe configured to perform a transient elastography measurement.

By measuring a viscoelastic property it is meant the complete set of steps of the method for providing a value of the property of the viscoelastic medium, from the step of calculating the property to the step of automatically selecting the optimum depth range.

By global measurement of a property of the viscoelastic medium it is meant repeating the measurement method previously defined on M measurements and achieving a global calculation of the value of the property. The global calculation can be performed using a mathematical function of the median or mean type applied to the values of the property the calculation of which is valid. By depth it is meant a direction of space extending within the viscoelastic medium of interest. For example, depth is the direction corresponding to the direction of propagation of the ultrasound emitted during the measurement of the property of the viscoelastic medium. When the medium is a human liver, the patient's skin corresponds to depth zero. Since the probe for elastography is in contact with the patient's skin, the distance skin-to-capsula of the liver corresponds to the probe-to-capsula of the liver distance.

By calculation depth range it is meant the depth interval within which the property is calculated. For example, if the viscoelastic property is measured using one or more ultrasound acquisitions, the calculation depth range is the region within which the ultrasound signals, detected and used to calculate the property, are reflected.

The step of calculating the value of a property of the viscoelastic medium may include a step of measuring by transient elastography comprising calculating an elastogram.

By elastogram it is meant the variation of a displacement parameter as a function of time and of the depth, representing the shear wave propagation in the viscoelastic medium.

The calculation step may also include a series of ultrasound acquisitions including the calculation of the distance between the probe and the wall delimiting the viscoelastic medium, each acquisition comprising emitting an ultrasound pulse and detecting on-the-fly the reflected ultrasound signals. During the calculation step, the value of the viscoelastic property can be calculated in one depth range or in several possible depth ranges.

By validity criterion of the depth range it is meant a criterion calculated from the distance between the ultrasound probe and the wall of the viscoelastic medium. This distance is also called "probe-to-capsula distance" or PCD.

A depth range is defined as valid if it does not include the wall or surface of the viscoelastic medium. For example, if the viscoelastic medium to be characterised is a human or animal liver, a depth range is defined as valid if it does not comprise the liver capsula. In other words, a depth range is defined as valid if it is entirely within the medium to be characterised.

By validity criterion of the calculation of the property of the viscoelastic medium it is meant a criterion established from an elastogram constructed from an ultrasound acquisition.

According to an embodiment, the validity criterion of the calculation of the property of the viscoelastic medium over a given depth range can take into account the quality of the shear wave propagation. It can correspond, for example, to the coefficient of determination of the linear regression obtained from the propagation of the shear wave represented in the elastogram (see article Ultrasound in Medicine and Biology, vol 29, number 12, 2003, page 3) or to the signal-to-noise ratio of the elastogram. In these cases, the calculation of the property is considered as valid in a given depth range only if the coefficient of determination or the signal-to-noise ratio is greater than a predetermined value.

If more than one depth range is valid, a selection criterion is applied to the values of the property the calculation of which is valid, to automatically choose the optimum depth range.

Beneficially, the method according to the invention enables to discard depth ranges which are not entirely within the medium to be characterised. In other words, the calculation of the property is automatically performed within the organ or medium to be characterised.

Beneficially, the method according to the invention enables to discard values of the property for which the shear wave propagation is of poor quality on the elastogram. The calculation of the speed of propagation of this shear wave is thus more reliable.

Beneficially, the method for automatically selecting the calculation depth range makes the measurement morpho-adaptive. Indeed, the depth range selected by the method according to the invention is automatically within the organ, independently of the patient's morphology.

Beneficially, the method for automatically selecting the depth range allows to avoid at least partially the dependence on the operator. In other words, the selection of the calculation depth range is no longer carried out by the operator.

Beneficially, by virtue of the method according to the invention, the measurement covers a larger zone of the viscoelastic medium to be characterised.

Beneficially, when the viscoelastic medium is an organ, for example a human or animal liver, the examination is faster, especially for patients with a large probe-wall distance of the organ or PCD.

If several depth ranges are valid, a selection criterion is applied during the selection step in order to choose a calculation depth range. There are several criteria for selecting the depth range.

The method according to the invention further comprises a step for determining the validity of the calculation of the property of the viscoelastic medium, this calculation being considered as valid if it fulfills a validity criterion calculated from the quality of an elastogram.

The depth range selection criteria are only applied to the values of the property the calculation of which is valid over at least one valid depth range.

The method is implemented at each new measurement M. Upon implementing the method, the number of calculations of the property of the viscoelastic medium is at least equal to 1, and at most equal to P.

During the step of determining the validity of the calculation depth range, the validity of each of the P depth ranges is determined for each new measurement M.

During the step of determining the validity of the calculation of the property of the viscoelastic medium, the validity of each of the calculations of said property is determined for each new measurement M.

According to an embodiment, the selection criterion is based only on the last measurement. In other words, the method according to the invention takes into account only information available at the time of the last measurement to select the depth range.

In this case, the depth range selected in the selection step may be the depth range for which the greatest signal-to-noise ratio is observed in the elastogram calculated.

According to an embodiment, the depth range selected in the selection step is the depth range in which the elastogram is of the best quality.

According to an embodiment, the depth range selected in the selection step is the depth range that fulfills a criterion calculated from the homogeneity of the medium. The homogeneity of the medium can be measured from the series of acquisitions of the ultrasound signal.

Beneficially, these criteria enable to select a depth range in which the shear wave propagates properly.

According to an embodiment, if the calculation of the property of the viscoelastic medium is not valid in one depth range, the next depth range is selected until a valid property calculation is obtained. If no valid property calculation is characterised as valid among all valid depth ranges, a new measurement is performed, otherwise at least one of the previous selection criteria has to be met. This allows a larger segment of the organ to be observed and the examination time to be optimised.

According to an embodiment, the selection criterion is based on the complete set of measurements made. In other words, the method according to the invention takes into account information available from the first to the last measurement to select the depth range.

According to an embodiment, the depth range selected in the selection step is that for which the greatest number of valid property calculations is obtained, among the M measurements made.

According to an embodiment, the depth range selected in the selection step is the depth range for which the dispersion of the M calculated values in each range is minimized. For example, the dispersion of the calculated values can be given by the interquartile range or by the standard deviation of the values calculated.

According to an embodiment, the depth range selected in the selection step is that for which the best signal-to-noise ratio is obtained over the M elastograms calculated.

According to an embodiment, the depth range selected in the selection step is the range in which the calculated M elastograms have the best quality.

Beneficially, the quality of the elastogram reflects the good propagation of the shear wave in a depth range of the viscoelastic medium.

According to an embodiment, the depth range selected during the selection stage is that fulfilling a criterion calculated from the homogeneity of the medium.

The homogeneity of the medium can be measured from the ultrasound signal acquisition series.

The method for automatically selecting the depth range upon measuring a property of a viscoelastic medium according to the invention may also have one or more of the following characteristics, considered individually or in any technically possible combinations:

- each depth range is delimited by a first depth and a second depth and the depth range is defined as valid if the distance between the probe and the wall delimiting the viscoelastic medium is less than the first and second depth;
- a calculation of the property of the viscoelastic medium is defined as valid in the depth range considered if it fulfills a validity criterion calculated from the quality of an elastogram;
- during the calculation step, the property of the viscoelastic medium is calculated in at least one of the P possible depth ranges;
- during the calculation step, the property of the viscoelastic medium is calculated from M measurements made in at least one of the P possible depth ranges, M being an integer number greater than or equal to 2;
- the criterion for selecting the calculation depth range is based only on the last measurement made;
- the depth range selected in the selection step is the depth range in which the calculated elastogram has the highest signal-to-noise ratio;
- the depth range selected in the selection step is the depth range in which the elastogram is of the best quality;
- the depth range selected in the selection step is that which fulfills a criterion determined from the homogeneity of the medium;
- the selection criterion is based on the complete set of measurements made;
- the depth range selected during the selection step is that which minimises the dispersion between the values calculated for the property during the calculation step;
- the depth range selected is that which maximises the number of valid calculations of the property;
- the depth range selected in the selection step is the range in which the calculated elastograms have the highest signal-to-noise ratio;
- the depth range selected in the selection step is that in which the elastograms are of the best quality;
- the depth range selected is that which fulfills a quality criterion determined from the homogeneity of the medium;
- if the depth range in which the value of the viscoelastic property has been calculated is not valid, the calculation of the property is performed for a deeper range;
- if, during the selection step, at least two depth ranges fulfill the selection criterion, the shallower range is selected;
- if, in the selection step, at least two depth ranges fulfill the selection criterion, the deeper range is selected;
- the validity criterion of the depth range is binary and can take a value corresponding to a valid depth range or a value corresponding to an invalid depth range;
- the validity criterion of the property calculation is binary and can take a value corresponding to a valid calculation or a value corresponding to an invalid calculation;
- the property of the viscoelastic medium is selected from a group comprising: elasticity of the viscoelastic medium, Young's modulus of the viscoelastic medium, speed of propagation of a shear wave within the viscoelastic medium, shear modulus, an ultrasound attenuation parameter or a combination of these properties;

the validity criterion of the depth range is a binary indicator being equal to 1 if the depth range is valid and equal to 0 if the depth range is not valid;

the validity criterion of the property calculation is a binary indicator being equal to 1 if the calculation is valid and equal to 0 if the calculation is not valid.

A second object of the present invention is a method of global measurement of at least one property of a viscoelastic medium. The global measurement method comprises a first step of automatically selecting the calculation depth range using the automatic selection method according to the invention. The values of the property of the viscoelastic medium calculated in the step of selecting the depth range are stored, for example in a memory.

The global measurement method further includes a second step of global calculation of the property value of the viscoelastic medium from the property values for which the calculation is valid at the selected depth ranges, the global calculation being performed using a mathematical function of the median or mean type.

The global calculation can be performed using a mathematical function of the median or mean type. According to an embodiment, the first step of automatically selecting the depth range is repeated for each new measurement, for the valid depth ranges and for the property values for which the calculation is valid.

In the case where the depth range selection is based only on the last measurement, the global property value of the viscoelastic medium is calculated as the median or mean of all the property values the calculations of which are valid, over the previously selected and potentially different depth ranges. At each new measurement, the selected depth range is independent of the previous ones.

In the case where the selection of the depth range is based on all the measurements made, the global value of the viscoelastic medium property is calculated as the median or mean of all the values of the property the calculations of which are valid, on the same depth range. The property of the viscoelastic medium is selected from a group comprising: elasticity, Young's modulus, shear modulus, shear rate within the viscoelastic medium, an ultrasound attenuation parameter or a combination of these properties.

A third object of the present invention is a device for measuring a viscoelastic property of a viscoelastic medium with automatic selection of the calculation depth range, said device comprising:

a probe for elastography;

calculation means comprising at least a memory and a microprocessor;

said device being constructed and arranged to:

Calculate, from the ultrasound signal acquired using the probe for elastography and the calculation means, the distance between the probe and the wall delimiting the viscoelastic medium;

Calculate, from the ultrasound signal acquired using the probe for elastography and the calculation means, the property of the viscoelastic medium in at least one of the P possible calculation depth ranges;

Determine the validity of at least one of the P calculation depth ranges, a calculation depth range being considered as valid if it fulfills a validity criterion calculated from the distance between the probe and the wall delimiting the viscoelastic medium;

Determine the validity of the calculation of the value of the property of the viscoelastic medium over the valid depth range or ranges, said calculation being considered as valid if it fulfills a validity criterion determined from the quality of an elastogram;

Select, among the valid depth ranges comprising at least one value of the property the calculation of which is valid, a depth range fulfilling a predetermined selection criterion;

Calculate, from the values of the property for which the calculation is valid at the selected depth ranges, the global value of the viscoelastic property, the global value being calculated using a mathematical function of the median or mean type.

Beneficially, the device according to the invention allows the measurement of a viscoelastic property of a viscoelastic medium by automatically selecting the optimal calculation depth range. The automatic selection of the depth range is performed using the depth range selection procedure according to the invention. This makes the measurement of the viscoelastic property reliable, reproducible and operator-independent.

The device according to the invention may also have one or more of the characteristics below, considered individually or in any technically feasible combinations:

the probe for elastography is a probe for transient elastography;

the device according to the invention and the calculation means are included in the probe for elastography;

the device according to the invention further comprises means for displaying results of the measurements. For example, the display means are configured to display the measured elastogram, the depth range chosen for the measurement and the value of the viscoelastic property measured.

LIST OF THE FIGURES

Further characteristics and advantages of the invention will be clear from the description thereof given below, which is indicative and in no way limiting, with reference to the figures among which:

Figure 6A:
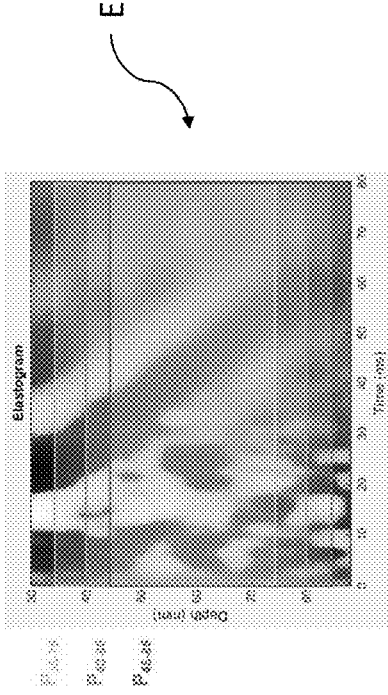
Figure 6B:
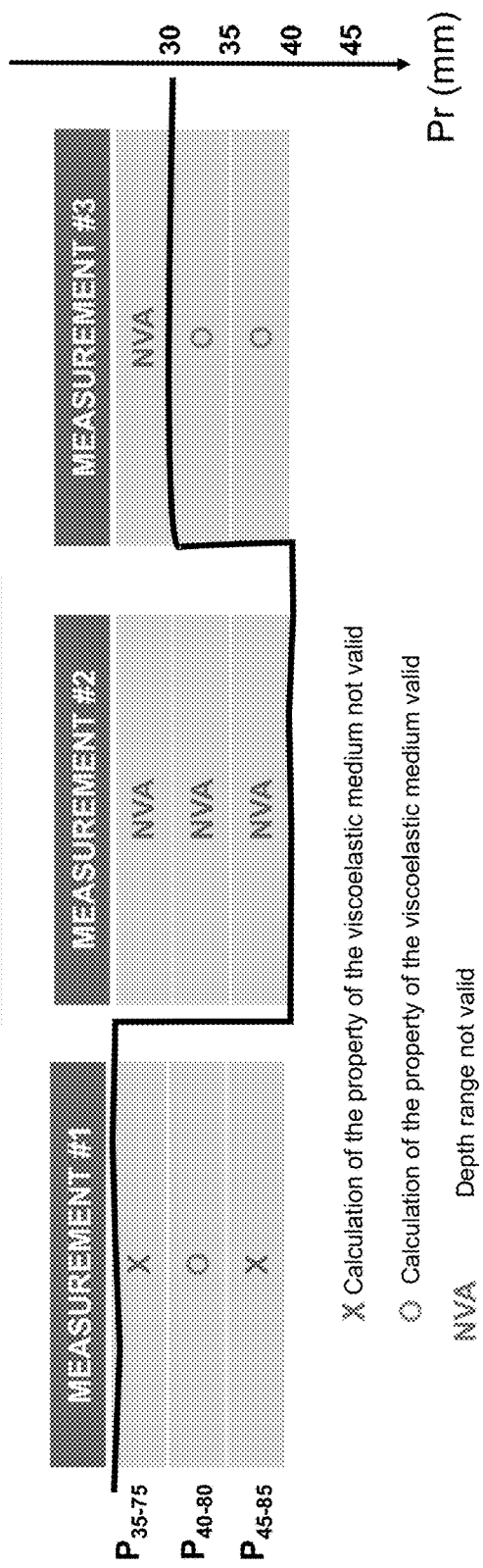
Figures 7A, 7B:
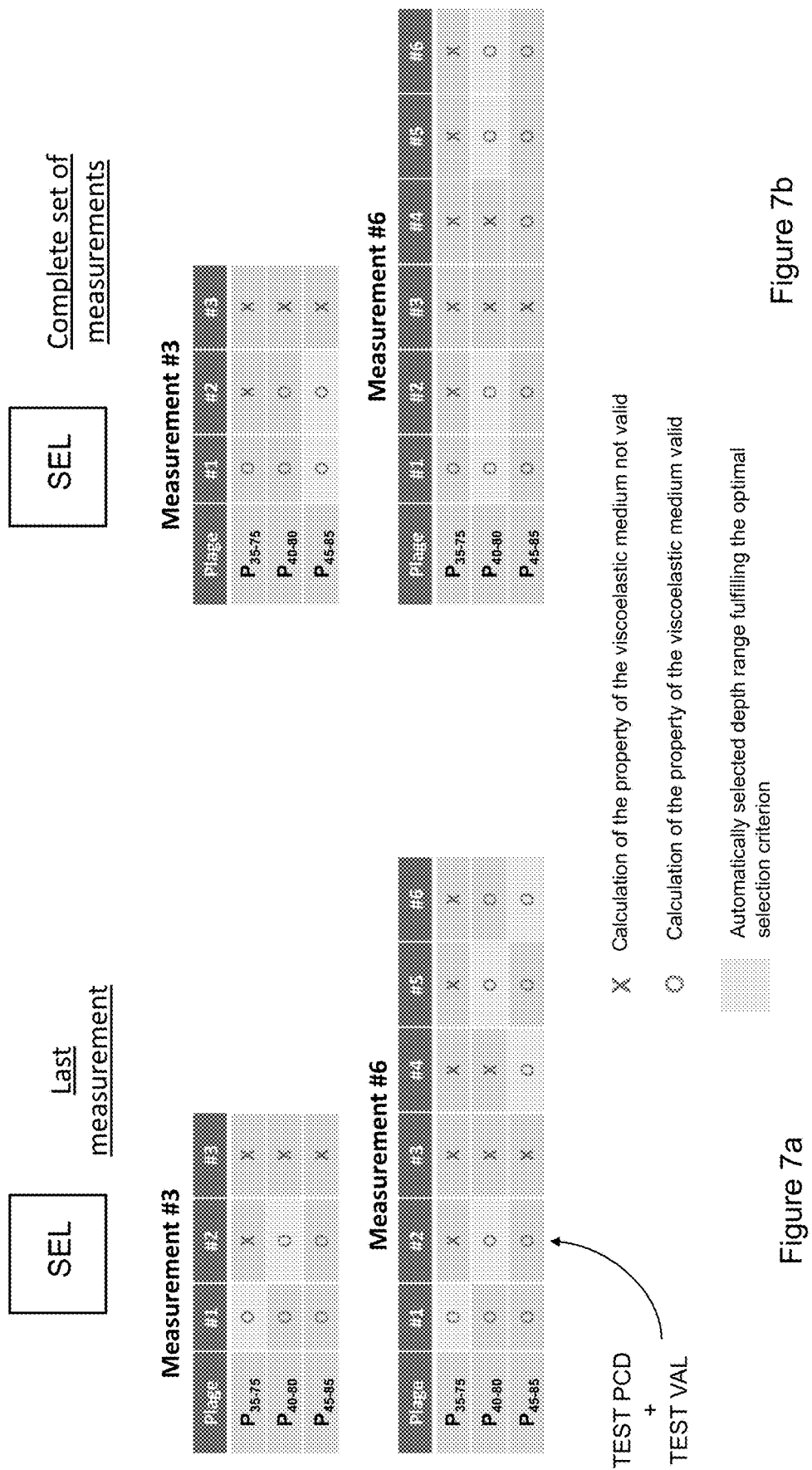
Figure 8:
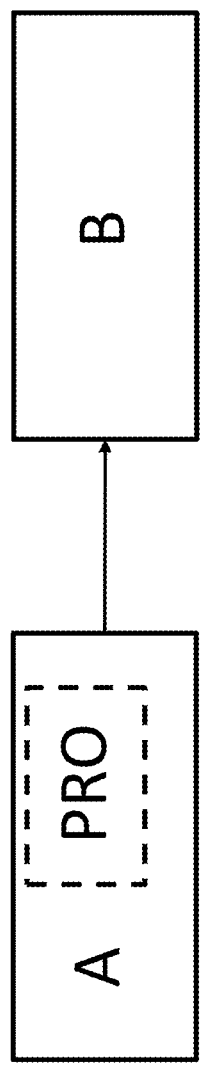
Figure 9:
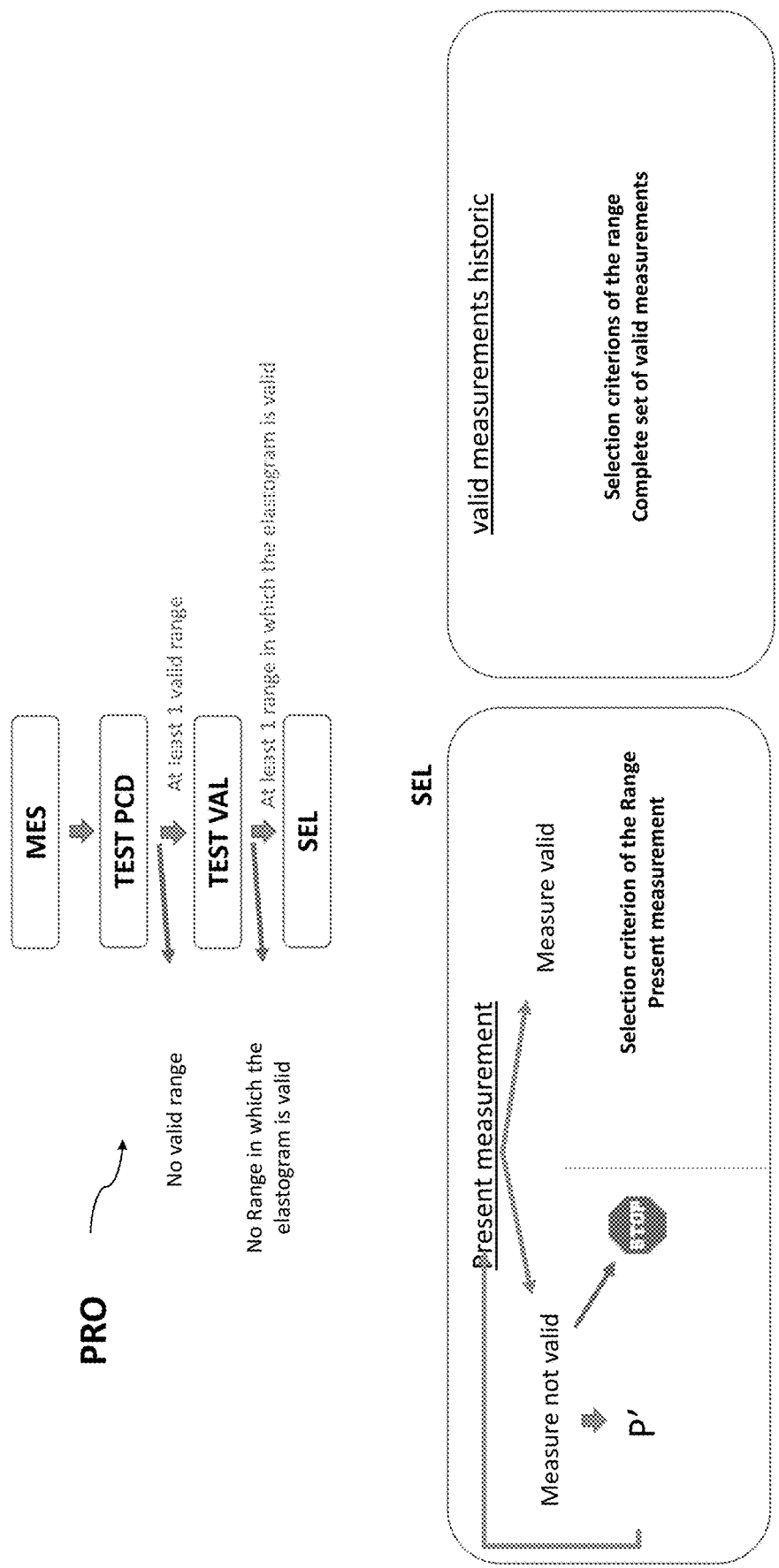

FIG. 3 schematically illustrates the steps of the method according to the invention;

FIG. 4 illustrates an optimal choice of the calculation depth range upon measuring a property of a viscoelastic medium according to the invention;

FIGS. 5a to 5d illustrate examples of validation of depth ranges for different probe-to-capsula distances PCD;

FIGS. 6a and 6b illustrate an example of validation of a calculation of the value of the property of the viscoelastic medium over P=3 depth ranges;

FIGS. 7a and 7b illustrate an example of validation of a calculation of a value of a property and automatic selection of the calculation depth range, the method according to the invention being implemented with P=3 possible depth ranges, wherein the validity criterion may be based on the last measurement only or on all the measurements made;

FIG. 8 schematically illustrates the steps of the method of global measurement of a property of a viscoelastic medium with automatic selection of the calculation depth range and the global calculation of the value of the property;

FIG. 9 summarises the method PRO for automatically selecting the calculation depth range according to the different selection criteria.

DETAILED DESCRIPTION

FIG. 3 schematically illustrates the steps of the method PRO according to the invention.

The method PRO according to the invention comprises the following steps:

A CALC step of calculating, from the ultrasound signal acquired using a probe for elastography, a viscoelastic property in at least one of the P possible calculation depth ranges. In this step the property can be calculated in a single depth range or in several depth ranges; during this step, the ultrasound signal acquired with a probe for elastography is used to calculate the distance PCD between the probe for elastography and the wall of the viscoelastic medium;

A step TEST_PCD of validating the calculation depth ranges in which the viscoelastic property has been calculated. A depth range is defined as valid if it fulfills a criterion calculated from the distance between the probe and the wall of the medium or "probe-to-capsula distance", PCD;

A step TEST_VAL of validating the calculations of the value of the viscoelastic medium property value over the valid calculation depth range or ranges. During this step, a validation criterion is applied to each calculation of the viscoelastic property to determine the validity thereof. A calculation is considered as valid if it fulfills a validity criterion calculated from the quality of an elastogram. For example, a calculation is considered as valid if the quality of the elastogram measured in the calculation depth range is sufficiently high. In other words, a calculation is considered as valid if the signal-to-noise ratio of the measured elastogram is sufficiently high;

A step SEL of selecting a depth range from the valid depth ranges including at least one valid calculation according to a selection criterion. The selection criterion can be based only on the last measurement made or all measurements made. In other words, if the calculation step CALC includes performing a single measurement, the selection criterion is based only on the last or current measurement. If the calculation step CALC includes making multiple measurements, the selection criterion may take into account the different measurements made, that is the history of measurements made.

These steps can be performed in the order shown in FIG. 3 or in a different order. The steps, all or part of them, can be performed in parallel.

According to an embodiment, the selection criterion for the calculation depth range is based only on the current measurement. In this case, the selection of the optimum depth range only takes into account information provided by the last measurement performed.

The depth range selected in the selection step SEL can be:
that for which the best signal-to-noise ratio is observed in the measured elastogram;
that for which the best propagation of the shear wave is observed on the elastogram, that is the best quality elastogram;
that for which the greatest homogeneity of the medium is observed.

Beneficially, these depth range selection criteria make it possible to select, among the depth ranges within the medium, the depth range in which the shear wave propagates correctly or that corresponding to a greater homogeneity of the organ.

According to another embodiment, the depth range selection criterion is based on the history of the measurements made. In this case, the selection of the optimum depth range takes into account information provided by all the measurements made.

The selected depth range can be:
that with the highest number of valid measurements among the M measurements made;
that for which the smallest dispersion between the calculated property values is observed among the M measurements made;
that which fulfills a criterion calculated from the homogeneity of the environment;
that for which the best mean or median signal-to-noise ratio is observed in the elastograms among the M measurements made;
that for which the best shear wave propagation on the elastogram is observed, that is the best mean or median quality criterion among the M measurements made;
that for which the greatest mean or median homogeneity of the medium is observed among the M measurements made.

The first CALC step includes calculating a property of the medium in at least one of the P possible depth ranges, the calculation being carried out from the ultrasound signal acquired by an ultrasound probe during a measurement. According to an embodiment, the calculation is repeated M times in at least one of the P ranges.

The measured property can be a viscoelastic property such as the speed of propagation of a pulse shear wave or the elasticity of the medium. In this case the measurement is a transient elastography measurement.

The measured property can be an ultrasound property such as a controlled attenuation parameter (CAP). In this case the measurement includes the generation of a series of ultrasound acquisitions.

During the step TEST_PCD, the validity of each calculation depth range is determined. Each calculation depth range is considered as valid only if the validity criterion fulfills a predetermined condition.

The depth range validity criterion can be binary and has a first value corresponding to a valid range and a second value corresponding to a non-valid range.

According to an embodiment, the depth range validity criterion is determined from the reflected ultrasound signal, over which the distance between the ultrasound probe and the wall of the viscoelastic medium is calculated. This distance is also called "probe-to-capsula distance" or PCD.

A depth range is defined as valid if it does not comprise the wall or surface of the viscoelastic medium. For example, if the viscoelastic medium to be characterised is a human or animal liver, a depth range is defined as valid if it does not include the liver capsule.

Beneficially, such a validity criterion makes it possible to keep only the measurements entirely included within the medium to be characterised.

During the step TEST_VAL, the validity of the calculation of the value of the property of the viscoelastic medium over the valid calculation depth range or ranges is determined. In other words, the validity of each of the calculated values is determined at each new measurement M. Each calculation is considered as valid only if the validity criterion fulfills a predetermined condition. The calculation validity criterion can be binary and has a first value corresponding to a valid measurement and a second value corresponding to a non-valid measurement.

According to an embodiment, the measurement validity criterion is defined from a pulse elastogram.

The elastogram is the image used to visualise the propagation of the shear wave during a pulse elastography measurement. The elastogram is defined by a two-dimensional matrix and provides a spatio-temporal representation of displacements generated by the propagation of the shear wave in the medium.

For example, the validity criterion can be established from the quality of the measured pulse elastogram. An estimate of the quality of the pulse elastogram can be provided by the signal-to-noise ratio of the pulse elastogram. The property values for which the calculation is valid are then the measurements with a pulse elastogram having a signal-to-noise ratio above a predetermined threshold.

A calculation of the property of the medium is automatically considered as invalid over an invalid depth range.

Beneficially, such a validity criterion makes it possible to discard measurements corresponding to a poor quality pulse elastogram, for example due to poor positioning of the probe or poor propagation of the transient shear wave within the viscoelastic medium.

During the step SEL, the optimum depth range is selected from the property value or values for which the calculation is valid. A depth range is defined optimal if it fulfills the best selection criterion imposed.

Beneficially, this step allows the automatic selection of the optimum depth range for measuring the property of the medium.

FIG. 4 illustrates the selection of the calculation depth range according to the invention when the viscoelastic medium is a liver F and the validity criterion of a depth range is determined from an ultrasound measurement, namely the probe-to-capsula distance PCD between the patient's skin S and the liver wall. The horizontal axis in the figure represents the depth Pr measured from the patient's skin S.

In the case illustrated in FIG. 4 the probe-to-capsula distance PCD measured by virtue of one or more ultrasound acquisitions is 38 mm.

The calculation depth range P has a lower bound Pi and an upper bound Ps. In the case of FIG. 4, Pi=45 mm and Ps=85 mm.

In order to obtain a valid depth range, the calculation depth range P is chosen so that its lower bound Pi is strictly greater than the probe-to-capsula distance PCD, Pi>PCD.

In other words, if Pi>PCD, the validity criterion takes the value corresponding to a valid depth range. Otherwise, the validity criterion takes the value corresponding to a non-valid depth range.

To increase the reliability of the validity criterion of a depth range, it is possible to introduce a transition zone Tr. The validity condition of a depth range in the depth range P then becomes: Pi>PCD+Tr.

In the example of FIG. 4 the transition zone has a thickness of 5 mm, Tr=5 mm.

Beneficially, the use of a validity criterion for a depth range defined from the PCD capsula probe distance ensures that the calculation depth range is entirely included within the medium to be characterised.

In other words, the use of a validity criterion for a depth range defined from the PCD probe-capsula distance enables measurement errors caused by the wall of the viscoelastic medium within the measurement zone to be avoided.

FIGS. 5a, 5b, 5c and 5d illustrate the validation of the measurement depth ranges of an elastic property of a liver F when three depth ranges are possible. The three depth ranges represented have depths comprised:
between 35 mm and 75 mm for P[35-75];
between 40 mm and 80 mm P[40-80];
between 45 mm and 85 mm P[45-85].

Figure 5A:
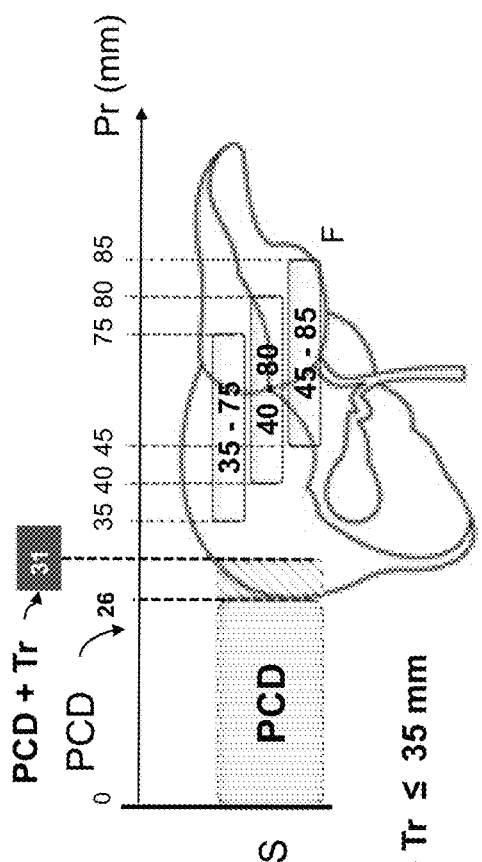

FIG. 5a corresponds to a probe-to-capsula distance PCD=26 mm. Using the quality criterion of a depth range illustrated with reference to FIG. 4, the result is that 35 mm>PCD+Tr, 35 mm being the lower bound of the shallower range. In this case all three depth ranges correspond to a valid depth range VA.

Figure 5B:
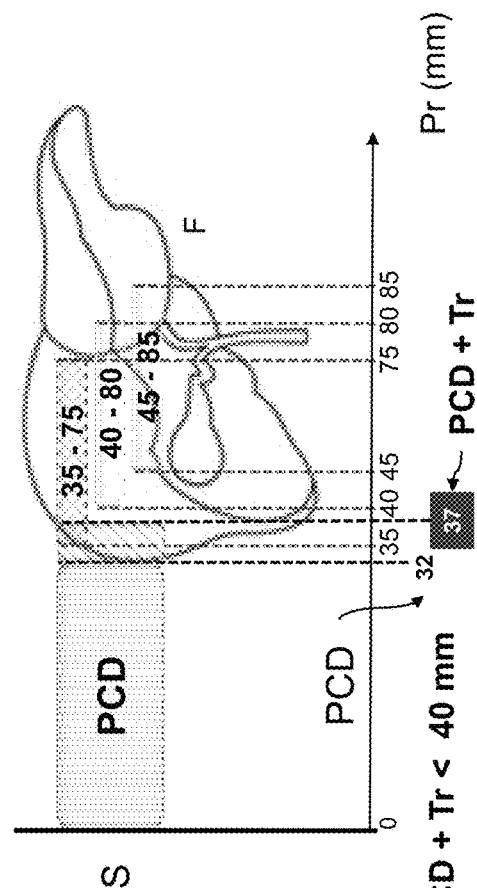

FIG. 5b corresponds to a probe-to-capsula distance PCD=32 mm. Using the quality criterion illustrated with reference to FIG. 4, the result is that 35 mm<PCD+Tr<40 mm. The depth range P[35-75] has a lower bound equal to 35 mm and therefore corresponds to a non-valid NVA depth range. This is due to the fact that the depth corresponding to PCD+TR=37 mm falls within the range P[35-75]. In other words, the measurement of a liver property made in correspondence of the range P[35-75] would be modified by the presence of the liver wall and the transition zone Tr. On the other hand, the depth ranges P[40-80] and P[45-85] correspond to valid depth ranges because they are entirely included within the environment F to be characterised.

FIG. 5c illustrates the case of a probe-capsula distance PCD=38 mm. The depth PCD+Tr=43 is greater than the lower bounds of the ranges P[35-75] and P[40-80]. These two depth ranges therefore correspond to non-valid NVA depth ranges. In the case illustrated in FIG. 5c, only the range P[45-85] corresponds to a valid VA depth range.

FIG. 5d illustrates the case of a probe-to-capsula distance PCD=60 mm. In this case, none of the depth ranges corresponds to a valid VA depth range.

FIG. 6a illustrates the step TEST_VAL of determining the validity of the calculation of the property value of the viscoelastic medium over the valid calculation depth range or ranges. For each measurement M, the calculation quality criterion is calculated in the valid depth range or ranges.

The validity criterion of a property calculation is established from a quality criterion of the pulse elastogram E.

FIG. 6b illustrates an example of validation of calculations of the values of a property of a viscoelastic medium in the form of a table, constructed from an elastogram such as that represented in FIG. 6a. The construction of a table such as that illustrated in FIG. 6b is an embodiment of the step TEST_VAL of determining the validity of each calculation of the property as a function of valid depth ranges.

The table in FIG. 6b illustrates the case of a sequence comprising measurements #1, #2, #3 for three possible depth ranges: P[35-75], P[40-80] and P[45-85].

The solid line represents the depth of the probe-to-capsula distance PCD+Tr at measurement #i.

The rows in the table show the binary validity results of the property calculations for each depth range P. The lower lines of each line correspond to the boundary depth at which the depth range becomes invalid. When the depth range is not valid, the property calculation validity criterion is not determined and is defined as invalid.

This table illustrates the validity conditions of the calculation of the value of a viscoelastic property according to the variation in PCD values.

The validity criteria of the property calculation in FIG. 6b are binary and can take two values "o" and "x". The value "o" corresponds to a valid calculation over a given depth range, the value "x" corresponds to a non-valid calculation.

The invalidity of a depth range is symbolised by the abbreviation "NVA", which means that the PCD capsule probe distance does not fulfill the following condition defined previously: Pi>PCD+Tr.

The property values of the validity criterion of the calculation show that measurement #1 is valid in the depth range P[40-80] and non-valid in the other two depth ranges P[35-75] and P[45-85] indicating poor quality of the elastogram.

The values of the depth range criterion indicate that measurement #2 is non-valid in all depth ranges. The position of the solid black line shows the presence of the liver capsule within the possible depth ranges when making the measurement.

The values of the validity criterion of the depth range show that measurement #3 is non-valid in depth range P[35-75], the shallower depth range. The non-validity of the calculation of property #3 in correspondence of the depth range P[35-75] is caused by the presence of the liver capsule in this depth range.

The steps of determining the depth range validity TEST_PCD and measuring TEST_VAL are typically performed using calculation means such as a memory and a microprocessor present in the device used to make the measurement.

The step SEL of automatically selecting the depth range fulfilling the optimal selection criterion when the selection of the optimal range is based only on the current measurement is illustrated in FIG. 7a.

FIG. 7a represents the case of repeated measurement M=6 times over P=3 possible ranges. The two tables represent the history of measurement validity criteria at the times of measurements #3 and #6 in the three depth ranges.

Each column represents the values of the validity criteria for the calculation of the value of the property of the viscoelastic medium calculated for a given measurement #i, each row corresponding to one of the three possible depth ranges.

Within a given depth range, a property calculation may be invalidated either because of an invalid depth range or by an elastogram quality criterion below a predetermined threshold.

For each measurement, the depth range is automatically selected independently of the previous measurements, and appears on a light background in the tables. From one measurement to the next, the history of selecting the optimum depth range does not change.

The mean or median value of the property of the viscoelastic medium is calculated from all the valid values of the property of the viscoelastic medium over potentially different depth ranges.

The step SEL of automatically selecting the depth range fulfilling the optimal selection criterion when the selection of the optimal range is based on the history or all the measurements is illustrated in FIG. 7b.

FIG. 7b considers the example of FIG. 7a again, representing the case of a repeated measurement M=6 times over P=3 possible ranges. The two tables represent the history of measurement validity criteria at the times of measurements #3 and #6 in the three depth ranges.

Each column represents the values of the validity criteria of a calculation of a property value calculated for a given measurement #i, each row corresponding to one of the three possible depth ranges.

Within a given depth range, a property calculation may be invalidated either because of an invalid depth range or by an elastogram quality criterion below a predetermined threshold.

For each measurement, the depth range is automatically selected and appears on a light background in the tables. From one measurement to the next, the history of the depth range selection is updated. The depth range selected from all previous measurements is replaced with the optimum depth range of the last measurement.

For example, at the time of measurement #3, the deeper depth range P[45-85] is selected for all measurements #1 to #3. At the time of measurement #6, the optimum selection criterion is met for the range P[40-80], which updates and replaces all previous range selections with the same depth range P[40-80].

The mean or median value of the viscoelastic medium property is calculated from all valid property values in the same depth range.

According to an embodiment, if two or more depth ranges provide the same optimal selection criterion in the SEL selection step, the shallower depth range is selected.

Beneficially, this allows the depth range closest to the ultrasound transducer and thus that with the highest signal-to-noise ratio to be selected.

Alternatively, according to another embodiment, the deeper depth range is selected.

Beneficially, this allows the depth range furthest from the liver capsule to be chosen.

The selection step SEL is typically performed using calculation means such as a memory and a microprocessor present in the device used to make the measurement.

FIG. 9 graphically summarises the steps of validating the depth range TEST_PCD, validating the calculation of the property value of the viscoelastic medium TEST_VAL and selecting the optimum depth range SEL.

According to an embodiment, the SEL selection of the optimum depth range is based only on the current measurement.

In another embodiment, the SEL selection of the optimum depth range is based on the history of the measurements made.

FIG. 8 schematically illustrates the method steps for the global measurement of a property of a viscoelastic medium with automatic selection of the calculation depth range, the automatic selection of the depth range being carried out using the method PRO according to the invention.

The measurement method comprises a first step A of automatically selecting the calculation depth range using the method PRO according to the invention. In step A, the measured values of the viscoelastic property are stored in a memory.

The global measurement method further includes a second step B of global calculation the viscoelastic property from the values calculated in step A. The global calculation can be performed using a mean or median type function.

According to an embodiment, in step B, the property of the viscoelastic medium is calculated from the values of the property for which the calculation is valid and which have been calculated in step A.

If the method PRO includes the performance of M measurements, the global calculation of the property of the viscoelastic medium is performed from the values of the property the calculation of which is valid and performed in the previously selected depth range or ranges. For example, the value of the property of the viscoelastic medium is the mean or median of the values of the property the calculation of which is valid and obtained over the selected depth range or ranges.

In practice, in the case of depth range selection based on the current measurement only, once the depth range of the last measurement is selected, the M measurements corresponding to independent depth ranges are used to determine the global value of the property measured. For example, the global measured value can be a mean of the values calculated corresponding to the selected range.

In the case of depth range selection based on the history of measurements made, once the depth range of the last measurement is selected, the property values of the M measurements corresponding to the last range chosen are used to determine the global value of the property. For example, the global value may be a mean of the values calculated in correspondence of the selected range. Beneficially, the global measurement method according to the invention makes it possible to improve reproducibility and reliability of the measurement of a viscoelastic property by selecting the property values the calculation of which is valid over the optimum depth range or over the optimum depth ranges for the measurement.

The measurements necessary for the implementation of the methods for automatically selecting a depth range and measuring a property of a viscoelastic medium according to the invention can beneficially be carried out within the scope of a transient elastography measurement using a device such as a Fibroscan®.

In this case the property of the viscoelastic medium is selected from a group of properties comprising: elasticity, Young's modulus, shear modulus, speed of propagation of a shear wave within the viscoelastic medium.

Figure 1:
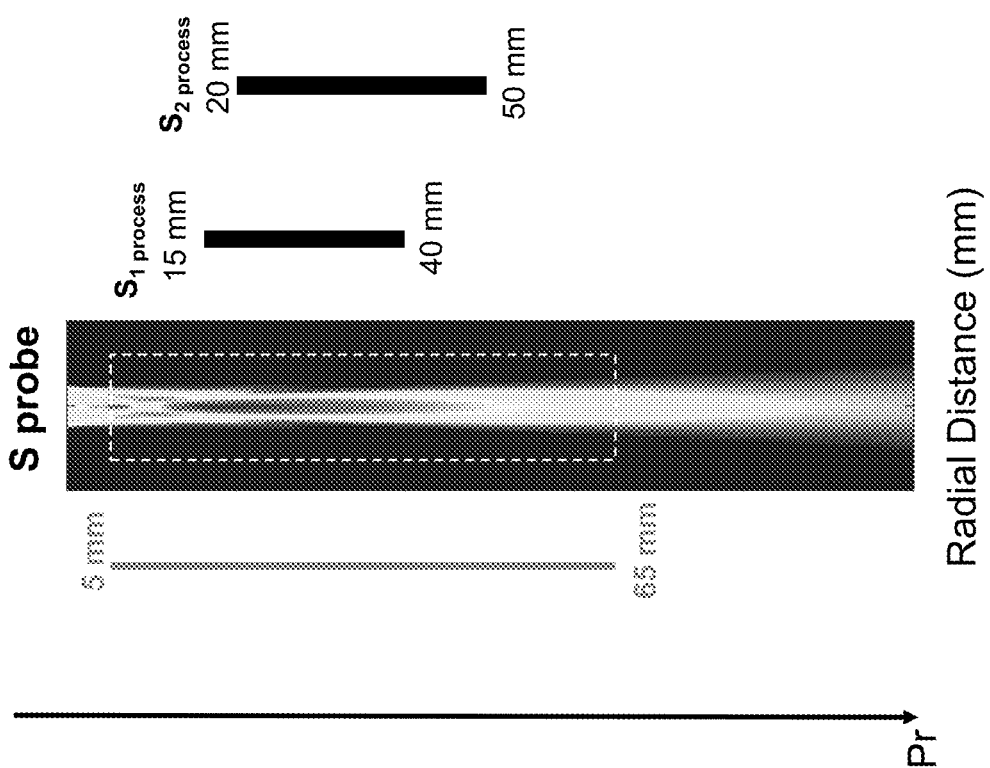
FIG. 1 illustrates the distribution of the acoustic power of ultrasonic waves propagating inside a viscoelastic medium of interest during a measurement of the transient elastography type, the operator being able to choose between two depth ranges S1 and S2.
Figure 2:
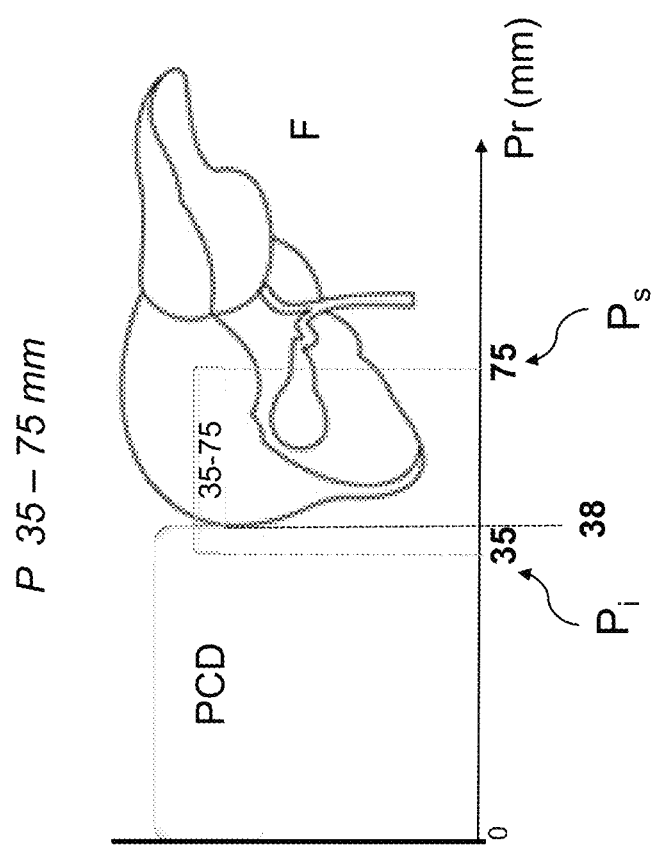
FIG. 2 illustrates the measurement of a property of a viscoelastic medium such as a liver according to the state of the art: the calculation depth range may include the wall of the medium.

The P possible ranges of calculation depth are set within the range of ultrasound acquisition depth in which the medium is observed. This observation zone depends on the properties of the probe used upon examining. As illustrated in FIG. 1, there are several choices of ranges P of measurement depths.

Each measurement M implementing the method PRO according to the invention includes monitoring the propagation of a transient shear wave within the viscoelastic medium to be characterised. To do this, during measurement #i, a transient elastogram E is constructed from the ultrasound signal acquired during the transient pulse elastography measurement. The elastogram E makes it possible both to measure one of the above-mentioned elastic properties and to determine a validity criterion of the property calculation within a defined depth range.

During the propagation of the transient shear wave, ultrasound acquisitions are generated with a high repetition rate to monitor the propagation of the transient shear wave. The reflected signals can also be used to determine the probe-to-capsula distance. The value of the probe-to-capsula distance makes it possible to calculate the validity criterion for a depth range.

The step of automatically selecting the depth range is performed using the calculation means included in the device used to make the transient elastography measurement. The calculation means include for example a memory and a microprocessor. The memory is configured to store the results of the M measurements made as well as the values of the various validity criteria calculated by the microprocessor.

The device used to perform the transient elastography measurement further includes means for displaying the results of the methods such as the selected calculation depth range or the property value of the viscoelastic medium.

Alternatively, the property of the medium can be an ultrasound attenuation parameter such as a controlled attenuation parameter (CAP).

A third object of the present invention is a device for measuring a property of a viscoelastic medium with automatic selection of the calculation depth range using the method according to the invention, said device comprising:
  a probe for elastography;
  calculation means comprising at least a memory and a microprocessor;
  said device being constructed and arranged to:
  Calculate, from the ultrasound signal acquired using the probe for elastography and the calculation means, the distance between the probe and the wall delimiting the viscoelastic medium (PCD);
  Calculate, from the ultrasound signal acquired using the probe for elastography and the calculation means, the property of the viscoelastic medium in at least one of the P possible calculation depth ranges;
  Determine the validity of at least one of the P calculation depth ranges, a calculation depth range being considered as valid if it fulfills a validity criterion calculated from the distance between the probe and the wall delimiting the viscoelastic medium (PCD);
  Determine the validity of the calculation of the property value over the valid depth range or ranges, a measurement being considered as valid if it fulfills a validity criterion determined from the quality of an elastogram;
  Select, from among the valid depth ranges including at least one valid measurement, a depth range fulfilling a predetermined selection criterion.
  Calculate, from the values of the property the calculation of which is valid made at the selected depth ranges, the global value of the viscoelastic property, the calculation being performed using a mathematical function of the median or mean type.

By probe for elastography it is meant a probe with at least one ultrasound transducer. An example of a probe for elastography is a probe for carrying out a transient elastography method.

The device is configured to implement the method for automatically selecting the calculation depth range according to the invention and calculating the global value of a property of the medium within the selected depth ranges.

According to an embodiment of the device according to the invention, the calculation means are included in the probe for elastography.

According to an embodiment, the device according to the invention further comprises means for displaying the results of the measurements. For example, the display means are configured to display the measured elastogram, the depth range chosen for the measurement and the measured viscoelastic property.

FIG. 9 summarizes the method PRO for automatically selecting a calculation depth range according to the invention.

During the step CALC, an ultrasound probe or a probe for elastography is used to calculate a property of the viscoelastic medium as well as the distance between the probe and the wall of the viscoelastic medium PCD. The property of the viscoelastic medium and the PCD are calculated from ultrasound shots emitted by the probe and ultrasound waves reflected by the medium and detected by the probe.

During the step TEST_PCD, the validity of the calculation depth ranges of the viscoelastic property is checked. A range is considered as valid if it is entirely included within the viscoelastic medium, that is if the distance from the probe to the medium wall is less than the bounds of the depth range PCD<Pmin.

According to an embodiment, if no depth range is valid, the calculation of the value of the property of the viscoelastic medium is performed at the next depth range. Alternatively, the method PRO is stopped.

During the step TEST_VAL, the validity of the calculations of the property values of the viscoelastic medium corresponding to the valid depth ranges is checked. A calculation is defined as valid based on the quality of the elastogram associated with the measurement.

In the step SEL, a depth range is selected from the valid depth ranges with at least one valid property calculation. The selection of the depth range is made according to a predefined criterion.

FIG. 9 illustrates two embodiments of the selection step SEL.

According to the first embodiment, the selection of the calculation depth range is based only on the current or last measurement performed. In this case, if several depth ranges include values of the property the calculation of which is valid, one of the following selection criteria is applied to select a depth range:

Best signal-to-noise ratio of the elastogram among all depth ranges;
Best shear wave propagation on the elastogram (quality criterion) among all depth ranges;
Best homogeneity criterion (LTT) among all depth ranges.
This embodiment is also illustrated in FIG. 7a.

In a second embodiment, the selection of the calculation depth range is based on the history or all the measurements made. In this case, the selected depth range is that fulfilling one of the following criteria:

Maximum of the number of values of the property the calculation of which is valid;
Minimum dispersion of the mean or median value of the property;
Best mean or median signal-to-noise ratio of the elastogram among all depth ranges;
Best shear wave propagation on the elastogram (mean or median quality criterion) among all depth ranges;
Best mean or median homogeneity criterion (LTT) among all depth ranges.
This embodiment is also illustrated in FIG. 7b.

The invention claimed is:

1. A method for automatically selecting a depth range for calculating a property of a viscoelastic medium, the depth range being chosen from P possible ranges, P being an integer number greater than or equal to 2, said method comprising:
   calculating, from an ultrasound signal acquired using a probe for elastography, the property of the viscoelastic medium in at least one of the P possible depth ranges and a distance between the probe and a wall delimiting the viscoelastic medium;
   determining a validity of at least one of the P calculation depth ranges, a calculation depth range being considered as valid if it fulfills a validity criterion calculated from the distance between the probe and the wall delimiting the viscoelastic medium;
   determining the validity of the calculation of the value of the property of the viscoelastic medium over the valid calculation depth range or ranges, said calculation being considered as valid if it fulfills a validity criterion calculated from the quality of an elastogram;
   selecting, from among the valid depth ranges comprising at least one valid calculation of the property of the viscoelastic medium, a depth range fulfilling a predetermined selection criterion.

2. The method for automatically selecting a depth range for calculating a property of a viscoelastic medium according to claim 1, wherein:
   each depth range is delimited by a first depth and a second depth;
   the depth range is defined as valid if the distance between the probe and the wall delimiting the viscoelastic medium is less than the first and the second depths.

3. The method for automatically selecting a depth range for calculating a property of a viscoelastic medium according to claim 1, wherein, during the calculating, the property of the viscoelastic medium is calculated from M measurements made in at least one of the P possible depth ranges, M being an integer number greater than or equal to 2.

4. The method for automatically selecting a calculation depth range for a property of a viscoelastic medium according to claim 3, wherein the selection criterion of the calculation depth range is based only on the last measurement made.

5. The method for automatically selecting a calculation depth range for a property of a viscoelastic medium according to claim 4, wherein the depth range selected during the selecting is that in which the elastogram has the greatest signal-to-noise ratio.

6. The method for automatically selecting a depth range for calculating a property of a viscoelastic medium according to claim 4, wherein the depth range selected during the selecting is that for which the elastogram is of the best quality.

7. The method for automatically selecting a depth range for calculating a property of a viscoelastic medium according to claim 4, wherein the depth range selected during the selecting is that which fulfills a criterion determined from the homogeneity of the medium.

8. The method for automatically selecting a depth range for calculating a property of a viscoelastic medium according to claim 3, wherein the selection criterion is based on the complete set of measurements made.

9. The method for automatically selecting a depth range for calculating a property of a viscoelastic medium according to claim 8, wherein the depth range selected during the selecting is that which minimises dispersion between the calculated values of the property.

10. The method for automatically selecting a depth range for calculating a property of a viscoelastic medium according to claim 8, wherein the depth range selected in the selecting is that which maximises the number of valid calculations of the property.

11. The method for automatically selecting a depth range for calculating a property of a viscoelastic medium according to claim 8, wherein the depth range selected during the selecting is that in which the elastograms calculated have the greatest signal-to-noise ratio.

12. The method for automatically selecting a depth range for calculating a property of a viscoelastic medium according to claim 8, wherein the depth range selected during the selecting is that for which the elastograms are of the best quality.

13. The method for automatically selecting a depth range for calculating a property of a viscoelastic medium according to claim 8, wherein the depth range selected is that which fulfills a quality criterion determined from the homogeneity of the medium.

14. The method for automatically selecting a calculation depth range upon measuring a property of a viscoelastic medium according to claim 1 wherein, if the depth range in which the calculation of the value of the property has been performed is not valid, the calculation is performed at a deeper range.

15. The method for automatically selecting a depth range for calculating a property of a viscoelastic medium according to claim 1, wherein if, during the selecting, at least two depth ranges fulfill the selection criterion, the shallower range is selected.

16. The method for automatically selecting a depth range for calculating a property of a viscoelastic medium according to claim 1, wherein if, during the selecting, at least two depth ranges fulfill the selection criterion, the deeper range is selected.

17. A method of global measurement of at least one property of a viscoelastic medium comprising:

automatically selecting the calculation depth range using the method according to claim 1;

performing a global calculation of the property of the viscoelastic medium from the values of the property for which the calculation is valid at the selected depth ranges, the calculation being performed using a mathematical function of the median or mean type.

18. The method of global measurement of at least one property of a viscoelastic medium according to claim 17, wherein the property of the viscoelastic medium is selected from a group comprising: elasticity, Young's modulus, shear modulus, shear rate within the viscoelastic medium, an ultrasound attenuation parameter or a combination of these properties.

19. A device for measuring a property of a viscoelastic medium with automatic selection of the calculation depth range using the method according to claim 17, said device comprising:

a probe for elastography;

a calculation unit comprising at least a memory and a microprocessor;

said device being constructed and arranged to:

calculate, from the ultrasound signal acquired using the probe for elastography and the calculation unit, the distance between the probe and the wall delimiting the viscoelastic medium;

calculate, from the ultrasound signal acquired using the probe for elastography and the calculation unit, the value of the property of the viscoelastic medium in at least one of the P possible calculation depth ranges;

determine the validity of at least one of the P calculation depth ranges, a calculation depth range being considered as valid if it fulfills a validity criterion calculated from the distance between the probe and the wall delimiting the viscoelastic medium;

determine the validity of the calculation of the property of the viscoelastic medium over the valid depth range or ranges, said calculation being considered as valid if it fulfills a validity criterion determined from the quality of an elastogram;

select, among the valid depth ranges comprising at least one valid property calculation, a depth range fulfilling a predetermined selection criterion;

calculate, from the values of the property for which the calculation of which is valid at the selected depth ranges, the global value of the viscoelastic property, the global value being calculated using a mathematical function of the median or mean type.

* * * * *